United States Patent [19]

Girerd

[11] Patent Number: 5,083,858

[45] Date of Patent: Jan. 28, 1992

[54] PHOTOBIOLOGIC SUNGLASSES AND TRANSMITTERS

[76] Inventor: René J. Girerd, 4 Gunston Ct., Morris Plains, N.J. 07950

[21] Appl. No.: 569,595

[22] Filed: Aug. 20, 1990

Related U.S. Application Data

[63] Continuation of Ser. No. 340,386, Apr. 17, 1989, abandoned.

[51] Int. Cl.$^5$ ............................................. G02C 7/10
[52] U.S. Cl. ..................................... 351/44; 351/163
[58] Field of Search ................... 351/44, 41, 49, 163, 351/165

[56] References Cited

U.S. PATENT DOCUMENTS

3,826,751  7/1974  Laliberte ............................ 351/163
4,783,361  11/1988  Ovshinsby et al. .................... 351/44

Primary Examiner—Paul M. Dzierzynski

[57] ABSTRACT

Sunglasses and other light transmitters for human viewing and illumination are characterized by an efficient transmission of photobiologically-active radiations, thereby offering the users (especially sunglass wearers) a physiologically-oriented alternative. Furthermore, the λmax and the peak absorbance wavelengths of human rhodopsin exemplify those wavelengths which must be transmitted, since they are photobiologically impeccable. Tinted photobiologic sunglass lenses transmit a light spectrum (FIG. 1) exactly within the human rhodopsin absorption curve (FIG. 2); they also provide antiglare as well as ultraviolet and infrared protection by attenuating radiations outside the photobiologic spectrum. Photobiologic sunglasses are also ecologically beneficial, restoring in part the pristine quality of the albedo which has been adulterated by modern urban enviroment. Specific photobiologic coatings provide various substrates with antireflection characteristics resulting in improved photobiologic transmission, and energy-saving infrared rejection. Tinting and coating are photobiologically cumulative. By transmitting the light which is most biologically active, photobiologic sunglasses and transmitters offer multiple health advantages over most prior-art sunglasses which interfere with photobiologic light and, consequently, have been reported to represent a significant health hazard. Therefore, photobiologic sunglasses and transmitters can help prevent some forms of mental depression (and the related increased suicide tendencies), a loss of fertility, as well as libido impairment, all caused by inadequate photostimulation. Maintenance of unperturbed mental and physical skills, of normal sleep, and of undisturbed metabolic functions, help maintain the well-being of photobiologically-stimulated sunglass wearers, and of photobiologic transmitter users.

1 Claim, 3 Drawing Sheets

PHOTOBIOLOGIC SUNGLASSES AND TRANSMITTERS

This application is a continuation of application Ser. No. 07/340,386 filed Apr. 17, 1989, now abandoned.

BACKGROUND—FIELD OF INVENTION

This invention relates to light transmitters, particularly to sunglasses and other aids to vision which are capable of efficiently transmitting desirable biologically-active light to the eyes, while providing antiglare and other protections.

BACKGROUND—DESCRIPTION OF PRIOR ART

Sunglasses were invented many centuries ago, independently by the Chinese and the Eskimos.

Originally, smoke-colored quartz lenses, which did not substantially impair vision, were worn by Chinese judges in court solely to conceal their eye expressions which, otherwise, might have unwittingly reflected their opinion before a trial's conclusion. When the first vision-correcting eyeglasses were introduced from Italy in 1430, the Chinese smoke-tinted them, not only to use them in court, but also to reduce solar glare.

Centuries ago, Eskimos handcrafted their own "sunglasses", solely from animal parts. These ivory goggles, with narrow horizontal slits in front of each eye, were highly effective against snow ophthalmia (an acute light-induced inflammation of the eyes) and resulting blindness, which occurred frequently in the spring, when an extremely strong sunlight is compounded by a snow albedo (reflection) of 75%.

The first "glass lentils" (so called because the early lenses looked like lentils) were invented during the 1280s in Pisa, Italy, by Salvino Armato, a Florentine optical physicist. Like the Eskimos' goggles, they were held by leather strips passing behind the ears. Temples were invented by Edward Scarlett, a London optician, in 1727.

In the 1930s, the U.S. Army Air Corps commissioned Bausch and Lomb, Inc. of Rochester, N.Y., to devise spectacles capable of protecting pilots' eyes from high altitude glare. Immediately, dark-green "aviator sunglasses", sold under the trademark RAY-BAN, became extremely popular as a novelty item, soon promoted by famous Hollywood stars. Such sunglasses were worn even in dimly-lit nightclubs, just to be chic, rather than for their antiglare characteristics. Since these sunglasses were made mostly for cosmetic appeal or privacy, they were simply made dark, without any other considerations in mind. These glasses thus blocked a portion of the light spectrum which is necessary to good health.

Since then, photobiology (the study of the biologic effects of light) became recognized as a science. Scientific data became available, which established that a portion of the light spectrum is essential to good health. In other words, since light is a primordial life-maintaining necessity, it is unwise to interfere with it by means of shaded or colored lenses, or transmitters, without due scrutiny and evaluation of the consequences upon human health.

But even today, sunglasses are designed and manufactured without any photobiologic considerations in mind. Consequently, and not surprisingly, prior-art sunglasses impair the transmission of photobiologic light, i.e., light which stimulates and preserves important bodily functions. Thereby such sunglasses insidiously interfere with a delicate "internal clock", which regulates most of our physiological functions. Recently, some French researchers have observed that mental alertness, sleep, and libido are severely disturbed among habitual users of dark sunglasses. This represents a major drawback inherent to the prolonged use of prior-art sunglasses and light transmitters.

Therefore readers may wonder why light is not included among the other basic necessities (food, water, and air) which are strictly protected by various law-enforcing agencies. Perhaps this could explain why eyeglasses and other light transmitters have never been challenged—let alone assessed—for their physiological impact upon users.

Ironically, the previously-cited Eskimo "sunglasses" managed to control effectively the luminance (intensity), without altering the color (quality) of the transmitted light, thereby offering a distinct advantage over most modern sunglasses.

Prior-art sunglasses offer only two basic options to the user: either neutral-density lenses, or tinted lenses. Both diminish light, including photobiologic light.

Most of today's users base their choice of sunglasses (non-corrective or corrective) primarily upon style, color, comfort, and antiglare characteristics.

Discerning users may prefer sunglasses capable of protecting the eyes against harmful radiations, such as ultraviolet (UV) rays. Regretfully, some currently available sunglasses with dark lenses are neither designed, nor tested, for adequate UV protection. Dark lenses which do not filter out UV radiations constitute a definite hazard beyond that of not wearing any sunglasses at all, since they induce pupillary dilation, thereby allowing more of the harmful UV radiations to penetrate the eyes. Fortunately, in 1987, the American National Standard Institute (ANSI) established a labeling code for UV protection, which knowledgeable users may follow to select sunglasses which eliminate a good proportion of the UV A [400 to 315 nanometers (nm)], UV B [315 to 290 nm], and UV C [290 to 200 nm] radiations. UV B and C radiations are considerably more penetrating, and hence more injurious to human living cells, than UV A radiations.

Heretofore, and except for providing optional ultraviolet protection, prior-art sunglasses have obviously not been designed with any medical considerations in mind, but arbitrarily, according to the preference of users who, so far, have never been offered physiologically-oriented alternatives.

Similarily, most prior-art light transmitters, such as clear prescription eyeglass lenses, windowpanes, windshields, and diffusers are not designed photobiologically; consequently, they lose some of the precious photobiologic light.

OBJECTS AND ADVANTAGES

Accordingly the following are some of the objects and advantages of my invention:

1. to provide sunglasses and light transmitters designed specifically with health integrity in mind;
2. to provide sunglasses, and other aids to vision, equipped with light transmitters which transmit the most photobiologically-active portion of the light spectrum to the users' eyes;
3. to provide photobiologic sunglasses and transmitters which are singularly suited to confer to the users a series of health advantages, due to an increased transmission of photobiologic light to the users' eyes;
4. to provide a desirable alternative to prior-art sunglasses which have been reported to be detrimental upon mental alertness and sexual activity, because they interfere with photobiologic light;
5. to provide sunglass users with significant glare protection; this is accomplished by the inherent rejection characteristics of the sunglass lenses for visible light radiations outside the photobiologic spectrum;
6. to provide sunglass users with ultraviolet and infrared protection; this is accomplished by the inherent rejection characteristics of the sunglass lenses for these harmful radiations;

Additional objects and advantages are:

7. to provide some selected users (such as urban dwellers) with ecologically-oriented eyewear, offering partial green-blue light spectrum rehabilitation, thereby compensating for man-induced environmental green-blue depletion;
8. to provide users with eyewear lenses, as well as light transmitters, diffusers, filters, shades, screens and other light transmitting devices which transmit more biologically-active light.

Other objects and advantages of the invention are to utilize the human rhodopsin absorption spectrum as a standard for the transmission characteristics of all photobiologic transmitters, including sunglasses.

Readers will find further objects and advantages of the invention from a consideration of the ensuing description, and of the accompanying drawings.

REFERENCE NUMERALS IN THE DRAWINGS

1—afferent light
2—efferent light
3—substrate
4—124 nm (or $\lambda/4$) thick coatings
5—sectional representation of the coated lens
6—lens
7—temple
8—afferent light
9—efferent light
10—substrate
11—124 nm (or $\lambda/4$) thick layer #1
12—124 nm (or $\lambda/4$) thick layer #2
13—afferent light
14—efferent light
15—substrate
16—124 nm (or $\lambda/4$) thick layer #1
17—248 nm (or $\lambda/2$) thick layer #2
18—124 nm (or $\lambda/4$) thick layer #3

TECHNICAL BACKGROUND

Prior to discussing the present invention, and in order to acquaint the reader with the field, I will first discuss its technical background, including ocular photobiology, melatonin, seasonal affective disorder syndrome, light and irradiance, rhodopsin, human interference with photostimulation, and coated light transmitters.

BACKGROUND—OCULAR PHOTOBIOLOGY

Those familiar with biology are usually aware of the sensory function of the retina: vision. However, even among those most skilled in physiology, very few regard photobiology as an important extrasensory retina-mediated physiologic mechanism. Photobiology is a complex science, and its implications are often unexpected.

An impressive body of scientific and medical data shows that extra-sensory photostimulation of the retina is an essential prerequisite for the proper development, and maintenance, of most bodily functions in all animal species, including humans. See, e.g., "The Science of Photobiology" by K. C. Smith, Plenum Press (1977), and "The Medical and Biological Effects of Light", Annals of the New York Academy of Sciences, vol. 453 (1985).

Over billions of years of evolution, the nycthemeral and seasonal rhythms have been used to implement specific adaptive mechanisms, which have insured the optimum survival of most existing animal species. The periodic variations of daylight duration and irradiance have been instrumental in the establishment of semi-independent internal, cyclic physiologic mechanisms (photoperiodicity, zeitgebers, oscillators, etc.), which govern the reproduction cycles of most species, and require appropriate ocular photostimulation (entrainment) to remain synchronized.

To be an effective stimulant, the light reaching the eyes must be adequate in terms of its quality (wavelengths), its quantity (irradiance and duration), and its distribution (daily rhythmic periodicity).

In most animal species, including man, nearly all the effects of photostimulation are mediated through the pineal gland, via the retino-hypothalamic tract and the suprachiasmatic nuclei. It is a photo-neuroendocrine transduction.

In addition to ocular stimulation, some birds (sparrow, mallard and Japanese quail), and a few newborn mammals, get significant extraocular photostimulation of the pineal gland (third eye) directly through the skull and brain. Some pineal glands have elementary photoreceptors reminiscent of retinal rods. In man, it has been stated that one, out of one million photons, may reach the pineal gland directly through the skull and brain. Brain tissue is known to be a relatively good light transmitter.

In most mammals, including man, the pineal gland produces and secretes its main hormone, melatonin, on a 24-hour cycle, in phase with the photoperiod. Plasma melatonin levels are at their lowest around noon, and peak around midnight. It appears that, when nature implemented the blueprints of the "melatonin clock", light was used as the inhibitor of choice to curb melatonin secretion. In most species, including man, photostimulation during the scotophase rapidly, and nearly completely, inhibits melatonin release. Some species, such as the cotton rat, need only a single one-second exposure to light during the scotophase to inhibit melatonin, thereby demonstrating that inappropriate light tampering may have unexpected consequences and should be avoided.

Constant light exposure, in the rat, results in a smaller pineal gland. Conversely, darkness causes hyperactivity and enlargement of the pineal.

It has been suggested that the melatonin clock could be regulated either by the duration of daylight, or by coincidence of the photoperiod with a separate circadian rhythm of sensivity.

BACKGROUND—MELATONIN

Most of the effects of the melatonin hormone are inhibitory. In fact, melatonin and some tranquilizers, such as the benzodiazepines—some sold under the trademarks VALIUM and LIBRIUM (both available from Roche Products Inc., Manati, PR, 00701)—have identical effects. Normal young human volunteers receiving exogenous melatonin have reported the following symptoms: sleepiness, fatigue, confusion, depression, and impaired judgement. Melatonin has been implicated in several other behavioral and mental derailments, because of its close structural kinship to serotonin, and to other psychomimetic molecules.

Jet lag reflects an internal physiologic dissociation from the external conditions, which results in desynchronized sleepiness or alertness, hunger or satiation, as well as mental and physical impairment. Five mg of melatonin will help re-establish the sleep pattern, as well as the other disturbed physiologic rhythms. Jet lag can also be treated by phototherapy.

Melatonin inhibits sexual maturation and gonadal activity in most animal species. For instance, in man, melatonin blood levels remain high until puberty; when they fall, puberty occurs. Children who have no more melatonin due to a destructive pineal tumor have a precocious puberty. Sperm mobility and fertility in man are both depressed by melatonin. In women, morning plasma melatonin levels bottom out during the peri-ovulatory phase of the menstrual cycle, and reach a maximum during menstruation. The bimodal pattern observed in human births correlates with the seasonal changes in the photoperiod, and in melatonin levels. Some hormonal and metabolic derailments, such as Mendenhall syndrome (familial pineal hypertrophy with diabetes mellitus), have been linked to melatonin.

BACKGROUND—SEASONAL AFFECTIVE DISORDER SYNDROME

This syndrome affects 5,500,000 individuals in the United States of America. It is characterized by mental depression occuring annually, from December through February in the northern hemisphere, and from June through August in the southern hemisphere. It is associated with hypersomnia, loss of libido, a craving for carbohydrates, and an increased suicide rate. It is solely due to insufficient photostimulation and, consequently, it is cured by carefully scheduled phototherapy sessions, using bright light.

BACKGROUND—IMPORTANCE OF LIGHT AND IRRADIANCE

Since melatonin is, by large, a sedative which is suppressed by light, it is clear that light acts as a stimulant. Consequently, light should not be curtailed indiscriminately.

The benefits of heliotherapy have been known since ancient Greece. A strong irradiance (phototherapy) cures Seasonal Affective Disorder Syndrome, explaining why patients with this syndrome improve when they travel towards the equator.

Rats exposed to constant light develop larger testicles. A single, daily, one-second exposure to light, during an experimental protracted period of darkness, suffice to maintain the gonadotrophic stimulation which, otherwise, would remain inhibited. In addition, constant light exposure increases the longevity of cardiopathic hamsters.

Phototherapy, in human neonates, is known to increase gonadotrophic levels. The level of ambient illumination has been shown to alter arousal in humans. Schizophrenia could be etiologically related to an altered sensivity to light exposure.

BACKGROUND—RHODOPSIN AND PHOTOBIOLOGY

In all species endowed with visual color perception, the retina has two types of photoreceptor cells: the cones (three million per human retina) which mediate high-definition color vision in bright light; and the rods (one hundred million per human retina) which permit black and white vision in dim light (scotopic vision), as well as photobiologic stimulation. However, most physiologists equate rod function with scotopic vision and, thereby, tend to forget that ocular systemic photostimulation is solely rod-mediated, and important.

The rods contain rhodopsin, a pigment better known as "visual purple". Rhodopsin is a very elaborate molecule which is capable of responding to a single photon (or quantum) of light, thereby triggering a cascade of reactions resulting in the amplification (100,000 times), and transduction, of the photic stimulus into a neuronal impulse. A part of the rhodopsin molecule, known as 11-cis retinal, is extremely stable (about 3,000 years), isomerically, in the dark. As part of the rhodopsin molecule, it is nested in the center of a 7-helix protein which acts as a "tuner", determining the spectrum of radiation (and, therefore, also the "peak" of the spectrum, known as the $\lambda max$) which is best suited to trigger the crucial retinal isomeric transformation. Within picoseconds of the "capture" (resulting in absorption) of a photon, the 11-cis retinal is changed into all-trans retinal (its isomeric form), causing a structural rotation of its molecular chain. The all-trans retinal immediately activates the opsin (the protein moiety of rhodopsin) which itself activates a phosphodiesterase, which opens the molecular ring of 3',5' cyclic guanosine monophosphate (GMP). Then GMP initiates the neurogenic transduction. This series of extremely rapid events is known as the cyclic GMP cascade of vision. Although this rod-mediated process accounts for dim light perception (non-color threshold vision), it is often forgotten that it is the only one responsible for transocular systemic photobiologic stimulation. Since it will respond to a single photon, it is, by far, the most sensitive physiologic mechanism in the human body.

Like other retinoid pigments, rhodopsin has an absorption curve peaking at a specific wavelength ($\lambda max$), which is slightly different for each species. Rhodopsin $\lambda$ max is best measured in situ, using a microspectrophotometer to explore the retina by means of a microbeam. Some optical characteristics of the eye media, such as light transmission, may vary with individuals and their age, explaining the differences observed. These differences are reminiscent of those previously reported for the λmax of human iodopsin, the pigment of the cones. In humans, rhodopsin absorption spectra are identical for both sexes.

Human rhodopsin λmax has been reported to occur at 496.3±2.3 nm. Most values in the literature are in the vicinity of 500 nm. It has been observed that ten times more photons are required at 360 nm than at 500 nm to suppress melatonin. Wavelengths in the 500 nm range are therefore, by far, the most effective initiators of the transocular photo-neuroendocrine transduction. This has been supported experimentally, in human volunteers, who were exposed to six different wavelengths of monochromatic light of identical irradiance during the scotopic phase of the photoperiod. The wavelengths used were 448, 476, 509, 542, 574 and 604 nm, with a 10 nm half-peak for each of the six wavelengths. Melatonin suppression was respectively 12, 26, 64, 20, 16 and 8%. The light peaking at 509±10 nm, which was the closest to the λmax, produced the largest (64%) melatonin suppression. Therefore, it was the most active among the six. Taking the half-peaks into account, it shows that the spectrum between 499 and 519 nm was the most effective.

Many vertebrates have relatively close rhodopsin λmax: frog 520, cattle 498, rat 498, macaque 508 nm. The fact that they are close to 520 nm (which is the maximum solar spectrum at sea level) is regarded as the result of ecologic adaptation. For the same reason, the λmax of rhodopsin of deep-sea fishes (475 nm) has evolved toward the color of their environment.

The entire electromagnetic spectrum does not contain any wavelengths which are more photobiologically-active than those which activate rhodopsin, as confirmed by the above-mentioned experiment on human volunteers exposed to six different wavelengths. Rare mammals get some photobiologic stimulation from UV radiations (360 nm) due to an exceptional lucency of their eye media, and also to a special rhodopsin.

BACKGROUND—HUMAN INTERFERENCE WITH PHOTOSTIMULATION

Humans are the only creatures which can modify and regulate at will the characteristics, duration, and distribution of their own exposure to light.

Most civilized humans prefer a lighted environment during wakefulness. The subsequent biologic impact of this protracted light exposure depends upon the phase of the photoperiod, the irradiance, and also, individual light sensitivity. Importantly (especially for sunglass wearers), this sensitivity to low light levels in the scotophase is itself altered by the intensity and duration of the light during the photophase. This means that, if the light reaching the eyes during the photophase is insufficient in terms of radiance, the "melatonin clock" will sense it as an inadequate stimulus, and will try to compensate by allowing very low light levels during the photophase to become effective melatonin inhibitors.

Insufficient melatonin levels during the photophase may perturb the photoperiodicity. Mentally depressed patients are among those known to be highly sensitive to melatonin suppression by light. But even among healthy sunglass wearers, idiosyncratic variations of sensitivity can be expected. Bright light during the photophase is probably the most effective circadian synchronizer.

By substantially diminishing the light reaching the eyes, most prior-art sunglasses will cause a diminished photoperiodic stimulation during the photophase; then a normally ineffective low light level during the scotophase (when sunglasses are not usually worn) will manage to inhibit melatonin, thereby causing further photoperiodic disturbances. Such low light levels are produced by artificial lighting, as normally exists in a house.

Although artificial lighting has benefited from a highly sophisticated technology, it has never been permeated by photobiology (except for phototherapy).

Sunlight is taken for granted today, in the same manner as other primordial necessities (such as air, water, and food) were one century ago. When some "air pollutants", such as chlorofluorocarbons, alter our atmospheric ozone layer and cause an undesirable increase in UV B irradiance, they become de facto genuine "sunlight pollutants" since they alter the pristine quality of our solar spectrum. Similarly, some prior-art sunglasses, by interfering with the adequacy of the light reaching the eyes, should effectively be regarded as individual light-polluting devices.

Consequently, the use of most prior-art sunglasses could prove as unwarrantable as the release of sulfur dioxide in the air, or the addition of nitrites in food products. Therefore, ideal sunglasses should not have this disadvantage and should not adulterate the portion of the light spectrum which is known to be beneficial.

Furthermore, another kind of man-made light pollution pertains to the impact of man's changing environment upon the spectrum of the reflected light thereof, with an albedo of about 15%. During eons of evolution, man's environment was mostly green (lush vegetation) and blue (sky). The resulting albedo was therefore shifted towards green-blue, possibly explaining why rhodopsin λmax is not at 520 nm, but near 500 nm. In an urban environment (buildings, sidewalks, asphalt, etc.) green is rare and the sky is often hardly visible, so that the reflected light has lost its original quality. It is therefore another advantage of the invention to provide urban users with a rehabilitated light quality (around 500 nm), closer to that of man's original habitat.

Since the effects of human-induced disturbances upon light are very variable and not immediate, it is very hard to establish a cause-effect relationship. However, as stated, in France, some psychologists have noted that dark sunglasses impair mental efficiency, while some sexologists have reported a clear loss of sexual performance among users of dark sunglasses. Another expert, professor Hervouet, has issued warnings since he believes that dark sunglasses present a serious health problem.

By curtailing photostimulation, prior-art sunglasses are apt to induce or aggravate the following conditions: seasonal affective disorder syndrome; behavioral abnormalities; hypersomnia; sleep disturbances; mental depression; suicide tendencies; decreased fertility and libido impairment.

Ideal sunglasses should control excessive glare, as well as protect the eyes against the harmful effects of some electromagnetic radiations, without interfering with systemic photostimulation.

BACKGROUND—COATED LIGHT TRANSMITTERS

In the air, and at ordinary ambient temperatures, all polished, transparent substrates which are covered by optical coatings with a different refractive index than that of their respective substrates acquire entirely different reflectance and transmittance characteristics for light. These new characteristics depend upon numerous factors, namely: the refractive index, the transmission properties, and the optical homogeneity of the substrate, as well as those of the coating substance(s); the number of layers in the coating of each major opposing surface of the substrate; the thickness of the individual layers in the coating; the sequence in which the layers are applied; the conditions under which the layers are applied (temperature, vacuum, partial pressure of oxygen) during the evaporation-deposition procedure. These same conditions may also influence very significantly the adhesiveness and the hardness of the layers, as well as the refractive index of some of the deposited substances, such as silicon monoxide.

Some relatively simple coatings may be used specifically to alter the reflectance, (and, consequently, the transmission) of a substrate; they are known as "anti-reflection" coatings.

Figure 4:
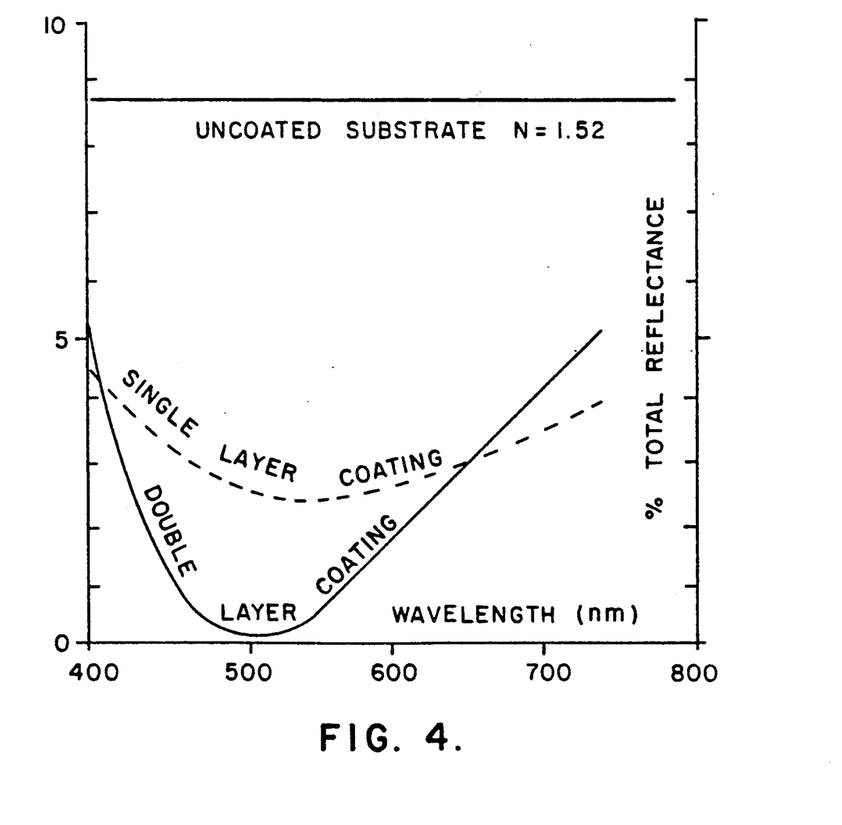
FIG. 4 shows the reflectance (and, consequently, the equivalent increased transmission) characteristics of three identical substrates: 1) without coatings; 2) with bilateral monolayer coatings; 3) with bilateral double-layer coatings.

A transparent, uncoated substrate with two major, polished, parallel surfaces, such as a clear eyeglass lens, may lose more than 8% (4% at each air-substrate interface) of the incident light through reflection (FIG. 4). The reflectivity, which is proportional to the refractive index of the substrate, is given by the Fresnel coefficient:

$$R = \frac{(n_o - n_s)^2}{(n_o + n_s)^2}$$

where:

$n_o$ is the refractive index of the incident medium (usually air).

$n_s$ is the refractive index of the substrate.

The above Fresnel coefficient applies to normal incidences. It also applies to oblique incidences, as long as the appropriate effective indices are used, instead of $n_o$ and $n_s$.

The reflectivity of a unilateral single-layer-coated substrate is:

$$R = \frac{(n_o - n_s)^2 \cos^2 \phi + (n_c - n_o n_s/n_c)^2 \sin^2 \phi}{(n_o + n_s)^2 \cos^2 \phi + (n_c + n_o n_s/n_c)^2 \sin^2 \phi}$$

where:

$n_o$ and $n_s$ are defined as just above.

$n_c$ is the refractive index of the coating.

$\Phi$ is the angle of incidence of the light.

In the 500 nm range, a bilateral ¼ wavelength coating can eliminate between 75% and 95% of the reflective at light incidences of 90° and 60° respectively; that is for a substrate like crown glass (n=1.52), and a coating such as magnesium fluoride (n=1.38).

Figure 5:
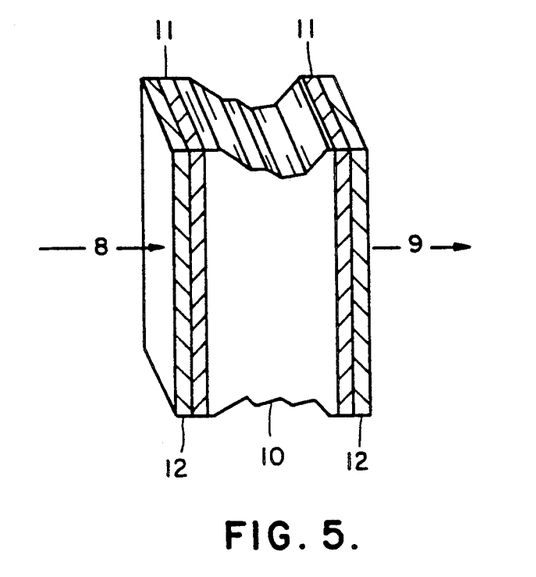
FIG. 5 shows a light transmitter with a double-layer coating on each major surface.
Figure 6:
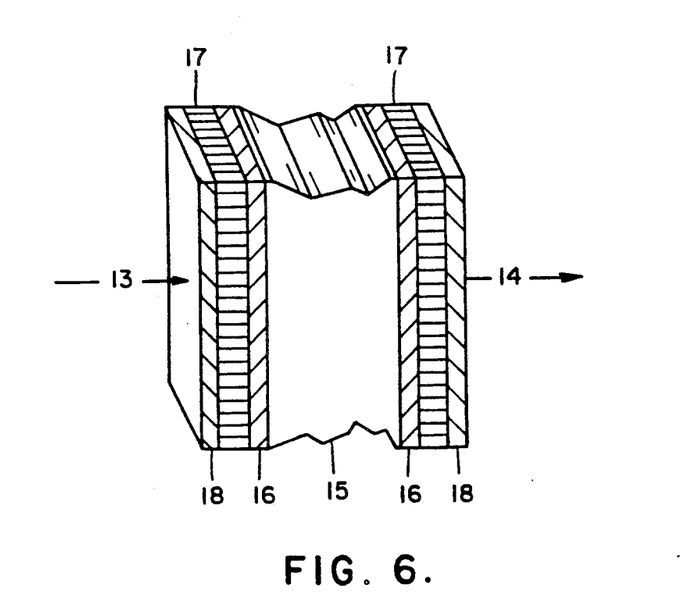
FIG. 6 shows a light transmitter with a triple-layer coating on each major surface.

When more than one layer (each having a different refractive index than its immediate neighbor) are deposited, one on top of another, on an appropriate substrate FIGS. 5 and 6), the overall reflectivity and transmission will vary very widely according to the number of layers, their individual thickness, and their sequential distribution. Some of these elaborate multilayered coatings may be utilized to change dramatically the transmission characteristics of a substrate; the substrate and the multilayered coatings then become a distinct, complex optical system. They act like "syntonized tuners" which, due to built-in reflectance zones, reject some wavelengths and transmit very narrow light spectra. They are usually delicate and are laborious to manufacture.

SUMMARY

In accordance with the invention, I provide sunglasses and other light transmitters which efficiently transmit photobiologic light, while curtailing transmission of the rest of the visible spectrum, as well as that of the UV spectrum. The transmitted light is, therefore, unique, and ideally suited to induce optimum photobiologic effects.

Those light transmitters which are destined to become eyewear lenses are appropriatedly shaped and mounted in a variety of frames, the combination allowing the user to view exclusively, and safely, through the lenses, with both eyes simultaneously, in a comfortable manner.

PREFERRED EMBODIMENTS

I provide various specific embodiments of photobiologic light transmitters in accordance with the invention. Specifically the inventive transmitters can be fabricated by dip-dyeing, homogeneous coloring, coating, as well as by combinations of coloring and coating, as will be described by way of the following examples.

COLORED EMBODIMENTS

Example 1

Dip Dyeing

Dip-dyeing is a simple technique which results in a very satisfactory transmission for a photobiologic transmitter, if achieved in the following manner:

A transparent, 0.4 mm thick plasticized polyvinyl chloride sheet, such as GLASKLAR 12 gauge H 5 (available from American Renolit Inc., 135 Algonquin Parkway, Whippany, N.J. 07981), is dipped once, for 5 seconds, in a 15% solution of vinyl chloride-vinyl acetate vinyl alcohol terpolymer (UNCAR solution vinyl VAGH, available from Union Carbide Inc., 39 Old Ridgebury Road, Danbury, Conn. 06817-0001) in n-propylacetate (available from Eastman Kodak Inc., Rochester, N.Y., 14650) containing 0.1% of MACROLEX GREEN 5 B (available from Mobay Inc., 550 Belmont Ave., Haledon, N.J. 07508), an anthraquinone dye. Drying occurs in approximately one hour, without hazing.

Figure 1:
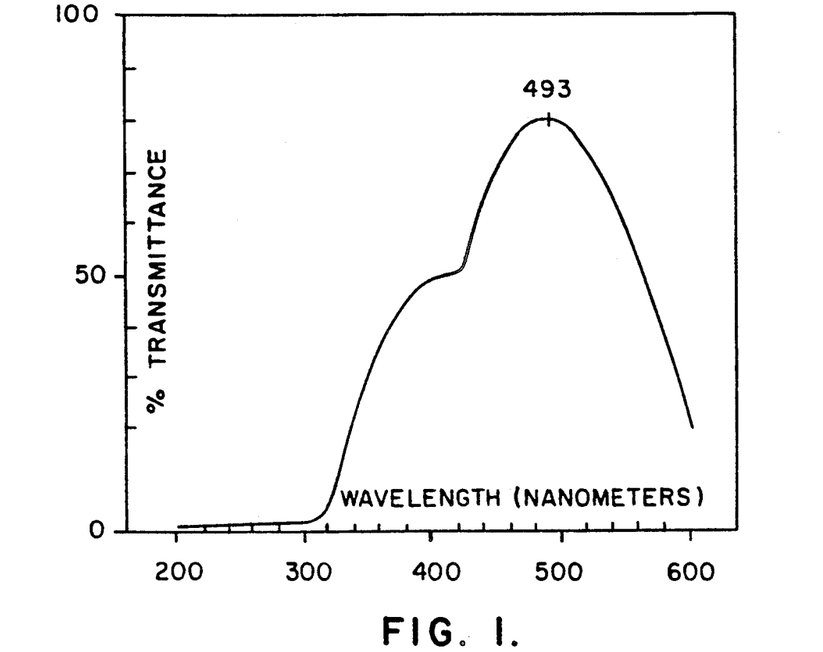
FIG. 1 shows a transmittance curve of light, as provided by sunglass lenses according to the invention, discussed in Examples 1 and 2 below.
Figure 2:
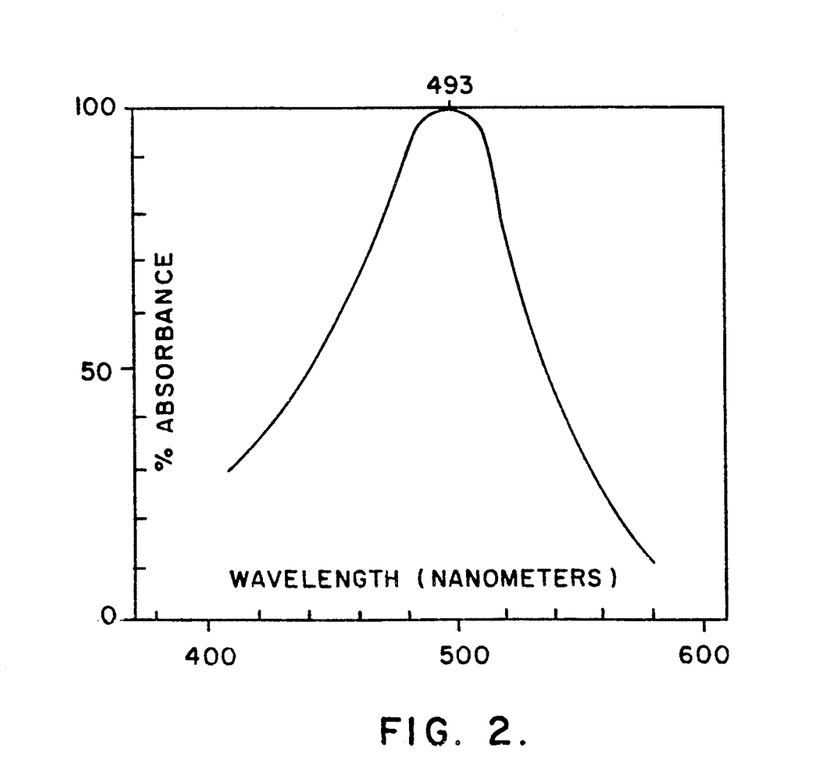
FIG. 2 shows a normalized absorbance curve of human rhodopsin, based upon Dartnall's monogram.

FIG. 1 shows the light transmittance of this embodiment as measured and plotted by a Beckman model 35 recording spectrophotometer (manufactured by Beckman Inc., 45 Belmont Dr., Somerset, N.J. 08873) over the full range of the instrument, i.e., from 200 to 600 nm. FIG. 1 also shows that the peak transmittance (80%) occured at 493 nm, which corresponds exactly to the λmax of human rhodopsin as shown in FIG. 2. The absorbance curve of FIG. 2 is the normalized spectrum of human rhodopsin based upon Dartnall's nomogram (as cited in "Some Properties of Solubilized Human Rhodopsin" by F. Crescitelli, Experimental Eye Research, vol. 40, p. 523, 1985). A comparison between FIG. 1 and FIG. 2 reveals that the transmittance curve of this embodiment is quite similar to the rhodopsin absorbance curve, a most desirable feature since it indicates that dip-dyed lenses transmit exactly in the photobiologic spectrum.

Readers can also note in FIG. 1 that the transmittance for other wavelengths in the visible spectrum outside the photobiologic range is comparatively low, thereby providing antiglare; for instance, transmittance for wavelengths below 420 nm and above 560 nm is less than 50%. Furthermore there is no measurable transmittance in the UV B and C spectra between 200 and 315 nm, indicating a total block of these radiations by the transmitter. Therefore this embodiment transmits effectively in the range of the human photobiologic spectrum, i.e., in the range where absorbance of human rhodopsin occurs; yet the embodiment also rejects radiations outside this range. As a result it provides total eye protection against these most damaging radiations which are now more intense than ever before due to the recent depletion of the protective ozone atmospheric layer.

Example 2

Substrate Coloring

Non-polar dyes, such as MACROLEX GREEN 5 B used above for dip-dyeing, are particularly well suited for direct incorporation in a plastic substrate, prior to the extrusion or lamination process. The resulting colored substrate has therefore transmission characteristics which are known to be identical to those obtained by dip-dyeing (FIG. 1).

Colored embodiments are best suited for sunglasses since the rejection of unwanted wavelengths is excellent, and since the color density of the lenses can easily be graded (to offer a choice of shades to the user) by varying the dye concentration during the manufacturing process.

COATED EMBODIMENTS

Example 3

Monolayer Coatings

A light transmitting substrate 3 (FIG. 3) can be bilaterally coated (coated on both sides) with one or several monolayers 4 to provide another simple embodiment of the invention. The layer (or coating) should, theoretically, be $496.3/4 = 124.075$ nm thick, since 496.3 nm is the value most often quoted in the literature for the $\lambda$max of human rhodopsin. However, in reality, it is virtually impossible to deposit layers with greater than a 1% precision so that they will, for all practical purposes, be referred to as 124 nm thick.

Figure 3A:
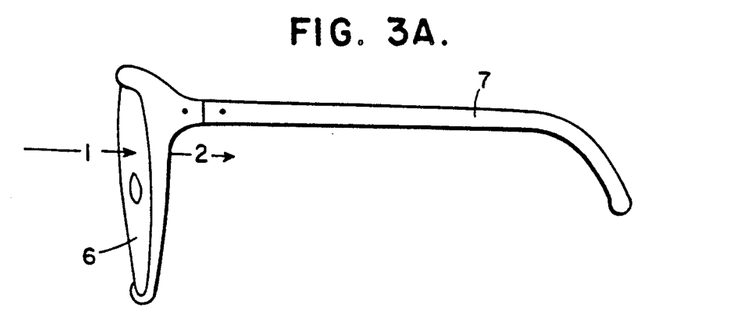
FIG. 3 shows a pair of photobiologic sunglasses, in which both lenses have a monolayer coating on each major surface.
Figure 3B:
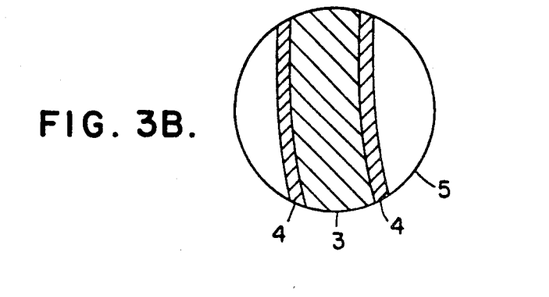

Such deposition is easily achieved by direct film deposition, via vacuum-evaporation when a substrate 3 is crown glass (n=1.52). Magnesium fluoride ($MgF_2$) is a preferred coating substance since it possesses a desirable refractive index (1.38) and yields a very hard, most durable coating.

Particles of $MgF_2$ (available from A. D. Mackay Inc., P.O. Box 1612, Darien, Conn. 06820) should, preferably, be no larger than 1 mm. Evaporation of $MgF_2$ is done by controlled resistance-heating in a vacuum chamber (available from Kurt J. Lesker Inc., 1515 Worthington Ave., Clairton, Pa. 15025). The vacuum should be approximately $10^{-5}$ mm Hg. The glass substrate must be adequately prepared by glow-discharge, and both the substrate and the vacuum chamber must be brought to 400° C. prior to deposition in order to remove water, as well as other adsorbed contaminants.

Substrates 3 can also be made of plastic, as well as other glasses and other known substrate materials. These are easily coated by low-temperature vapor-phase polymerization, yielding a polymer (such as parylene) coating 4. Parylene results from the polymerization of p-xylylene, in the absence of either high temperature, or high vacuum.

The starting material is p-xylene (available as dimethylbenze from Mallinckrodt Inc., P.O. 22648, St Louis, Mo. 63147). It is first heated with steam at 95° C. to produce di-p-xylylene, a solid, cyclic dimer which can be separated in pure form. This dimer is then pyrolyzed at 550° C. to produce a monomer-vapor of p-xylylene, which is then cooled below 50° C., and readily condensates on practically any substrate 3 as a polymer film 4 of high purity and uniformity, at or near room temperature, a distinct advantage. In this example, substrate 3 is polycarbonate (available from American Acrylics Inc., 4868 North Clark Street, Chicago, Ill. 60640). Layer 4 can be deposited with a precision of approximately 1% as has been verified with a microscope using the Michelson interferometer principle.

FIG. 4 shows the transmission characteristics of the bilaterally-coated embodiment of FIG. 3. The curve identified as "single-layer coating" shows, in percentage, the reflectance compared to uncoated substrate 3. The uncoated substrate reflects 8.75% of all wavelengths between 400 and 800 nm. In comparison, the coated substrate reflects between 2.5% (at 496.3 nm) and 4.5% (at 400 nm). This represents a 6.25% maximum differential in the 496 nm range. Since the light which is not reflected is transmitted through the substrate 3, the net gain brought by the coating is 6.25% at 496.3 nm, the most biologically-active portion of the spectrum. There is also a similar gain for the light frequencies immediately adjacent to 496.3 nm. At 400 nm the bilateral monolayer coating provides 4.25% (8.75–4.50) less reflectance (therefore 4.25% more transmission) than the same uncoated substrate.

All the above transmittance values are for normal (90°) incidences regardless of whether substrate is clear or tinted. They represent minimum values since for oblique incidences the transmission in the photobiologic range is even greater.

In addition, the 124 nm coating happens to be a good infrared reflector and thereby provides supplementary ocular protection to the user. This also represents a welcome energy-saving supplementary advantage for windowpane users by hampering heat transfer through the coated glass.

Coated clear prescription lenses transmit more photobiologic light without altering significantly the color of the transmitted light. The coating will also enhance further the photobiologic transmission of the colored sunglass lenses of Examples 1 and 2.

Example 4

Double-Layer Coatings

On a substrate 10 (FIG. 5) such as crown glass, a double-layer coating is applied by depositing a $\lambda/4$ thick (124 nm for a $\lambda$ of 496.3 nm) film 12 of silicon monoxide (SiO, available from A. D. Mackay Inc., supra), on top of a $\lambda/4$ thick (also 124 nm) layer 11 of $MgF_2$. This is done by vacuum evaporation-deposition just as described for Example 1. The refractive index of SiO layer 12 may vary between 1.4 and 1.9, according to the partial pressure of oxygen during the layer deposition. However, this does not materially alter the transmission characteristics of the coating. The thickness of the layers is verified spectroscopically.

On plastics and other substrates 10, double-layer coating is performed by depositing a polytetrafluoroethylene (sold under the trademark TEFLON from E. I. Du Pont de Nemours Inc., 1007 Market Street, Wilmington, Del. 19898) layer 12 upon a parylene layer 11, by means of low temperature vapor-phase evaporation-deposition, as indicated in Example 1.

FIG. 4 shows the reflectance of the double-layer transmitter illustrated in FIG. 5. Both major surfaces are coated. Each layer is 124 nm thick. The reflectance curve is identified as double-layer coating. The maximum reflectance is between 0.15% at 496 nm and 5% at 400 nm. This represents a differential of up to 8.6% when compared to the corresponding uncoated substrate. This means that the reflection of the photobiologic wavelengths at 496 nm (and adjacent wavelengths) is virtually eliminated. Since the light which is not reflected is transmitted through the coated substrate there is an 8.6% gain in the transmission of these photobiologic wavelengths.

The reader will observe from FIG. 4 that double-layer coatings are much superior to monolayer coatings in terms of transmission gain for specific wavelengths. For wavelengths far away from 496 nm, the reflectivity becomes even greater than that of the uncoated substrate. This reduces the transmission of these non-photobiologic radiations, and provides antiglare properties by rejecting them.

When used for clear prescription eyeglasses, double-coated lenses provide 8.6% more photobiologic light while confering some UV and infrared protection. Double-layer coatings can also be applied to some of the colored transmitters described in Examples 1 and 2, thereby increasing further the photobiologic transmission of these colored sunglass lenses.

Double-layer coatings (each layer having a thickness of ¼ of any photobiologic wavelength) confer specific, efficient transmission for this wavelength and are thereby consistent with the spirit of the invention.

Example 5

Triple-Layer Coatings

Triple-layer coated transmitters (FIG. 6) are better when made with a substrate 15 which has a low refractive index (1.5 to 1.7). The reflectivity of such transmitters is minimum when:

$$n_1 n_3 = n_0 n_s$$

and $$n_2^2 = n_0 n_s$$

where:
$n_0$ is the refractive index of the medium (air).
$n_s$ is the refractive index of the substrate.
$n_1$, $n_2$ and $n_3$ are the refractive indices of the 1st 16, 2nd 17 and 3rd 18 layers, respectively.

The best reflectivity, and therefore the best transmission, for 496.3 nm is obtained with the three following layers:
1st layer 16 and 3rd layer 18: $MgF_2$ (n=1.38), each 124 nm thick.
2nd layer 17: Zirconium dioxide (n=2.1), available from A. D. Mackay Inc., supra), 248 nm thick.

All layers are applied by evaporation-deposition exactly as indicated for Example 3.

In the 496.3 nm range, light transmission of this triple-coated transmitter was found to be virtually identical to that (illustrated FIG. 4) of the double-coated transmitter of Example 3. However, the triple-layer coating showed an improved reflectance at both ends of the light spectrum. Therefore it improves UV and infrared protection, when compared to the double-layer transmitter of Example 4.

Consequently, triple-layer coatings specifically made as described above are consistent with the scope of the invention, and can therefore be used on clear prescription lenses, or on sunglass lenses to provide additional photobiologic light, without appreciably changing the color of the transmitted light. They also provide significant UV and infrared rejection.

COMBINATIONS (COLORING-COATING)

Example 6

The colored substrate of Example 2 can be coated as indicated in Examples 3, 4 or 5. As formerly explained, the coatings provide up to 8.6% more photobiologic light which would not otherwise be transmitted due to reflection loss.

Therefore, the combinations represent most efficient embodiments since they provide more photobiologic light, as well as increased rejection characteristics for undesirable radiations. They provide the best photobiologic sunglass lenses.

VARIATIONS

Photobiologic sunglasses can be made with any of the above transmitter embodiments. However, the colored embodiments of Example 1 give a better rejection of undesirable non-photobiologic radiations. The color density of the lenses can easily be controlled by changing the dye concentration in the manufacturing process, to offer a choice to the users.

For ordinary sunglasses, the toric curvature of the inner surface of the lenses must match the toric curvature of the outer surface, so that the lenses are of uniform thickness and thus have zero power.

For those users who need optical eyewear correction, the lenses have vertical and horizontal meridians selected to provide the appropriate power corrections.

Color gradient lenses with a different color density at the periphery than at the center represent a variation of some of the above embodiments.

Colored contact lenses are sometimes used for cosmetic reasons. Green-blue "photobiologic" contact lenses could offer a cosmetic alternative, representing a further embodiment of the invention.

Coated prescription lenses provide users with up to 8.6% more photobiologic light as well as additional UV and infrared protection.

Coated transmitters are particularly well suited to transmit more photobiologic light through windowpanes, windshields and other daylight transmitters. They also reject efficiently unwanted wavelengths such as infrared and UV radiations. Consequently, those confined subjects who get their daytime illumination from the sun (either in a building or in a vehicle) will benefit from 8.6% more photobiologic light, while saving energy on either heating or air conditioning, since these coated transmitters hinder the transmittance (in and out) of heat-conveying infrared radiations.

SUMMARY, RAMIFICATIONS AND SCOPE

Accordingly, the reader will see that I have provided photobiologic sunglasses and other transmitters which transmit most efficiently the portion of the light spectrum which is essential to good health. Consequently, this very precious light can easily reach the user's retina to play its fundamental role. This is an advantage over most prior art sunglasses which often seriously handicap photobiologic transmission. As stated, photobiologic light is known to prevent and cure seasonal affective disorder syndrome, sleep disturbances, behavioral abnormalities, mental depression with associated suicide tendencies, decreased fertility, and libido impairment. Furthermore, the photobiologic transmitters offer additional advantages in that

- they provide sunglass users with glare protection, outside the photobiologic spectrum, which can be electively graded (during manufacture) according to either the color intensity of the substrate, or the number of layers in the coatings;
- they provide sunglass users with ultraviolet and infrared protection;
- they provide sunglass users with some ecological urban spectrum rehabilitation;
- they provide increased photostimulation to those users of prior-art sunglasses who may suffer from the effects of insufficient photostimulation;
- they provide users of clear prescription eyewear with up to 8.6% more photobiologic light;
- they provide users who get their environmental light through windowpanes or windshields with up to 8.6% more photobiologic light (16% if the same users are also photobiologic prescription eyeglass wearers);
- they provide users with windowpanes which also reflect heat-conveying infrared radiations, resulting in energy savings;
- they allow the utilization of antireflection coatings on colored substrates, resulting in cumulative photobiologic transmission;
- they allow light diffusers, transducers, filters, shades, screens and other light-transmitting devices to transmit more photobiologic light;
- they allow light producing devices (light bulbs, etc..) to emit more photobiologic light;

Although several embodiments of the invention have been disclosed for the purpose of illustrating the inventive concept, those of skill in the art will envision that minor changes in the transmission characteristics of the transmitters can be made without departing from the spirit of the invention. For instance, the peak transmission of a photobiologic transducer does not necessarily have to be at the $\lambda$max, as long as it occurs at a wavelength which is in the absorption curve of human rhodopsin. Thus the scope of the invention should be determined by the appended claims and their legal equivalents, rather than by the examples given.

I claim:

1. In the combination of:
    an optical filter having a substrate which has a pass-band transmission characteristic which peaks at about 495 nanometer wavelength and which drops rapidly in transmission on either side of the peak transmission to provide a transmission band from about 420 to 560 nanometer wavelength; and
    an antireflection interference lamina coated on said substrate;
    wherein the improvement comprises:
    having the indices of refraction of the lamina and said substrate and the thickness of said lamina selected so as to have a minimum reflection at the same said wavelength of about 495 nanometers,
    whereby the optical transmission of said combination at the same said wavelength of about 495 nanometers is maximized.

* * * * *